United States Patent
Angeli

(10) Patent No.: US 11,354,967 B2
(45) Date of Patent: ***Jun. 7, 2022

(54) PRECISION DISPENSER FOR LIQUIDS, COMPRISING A DEVICE FOR REMOTE CONTROL AND MONITORING

(71) Applicant: L. Molteni & C. dei Fratelli Alitti—Societa di Esercizio S.p.A., Scandicci (IT)

(72) Inventor: Roberto Angeli, Scandicci (IT)

(73) Assignee: L. Molteni & C. di Fratelli Alitti—Societa di Esercizo S.p.A.

( * ) Notice: Subject to any disclaimer, the term of this patent is extended or adjusted under 35 U.S.C. 154(b) by 0 days.

This patent is subject to a terminal disclaimer.

(21) Appl. No.: 17/135,371

(22) Filed: Dec. 28, 2020

(65) Prior Publication Data

US 2021/0118542 A1 Apr. 22, 2021

Related U.S. Application Data

(63) Continuation of application No. 15/446,809, filed on Mar. 1, 2017, now Pat. No. 10,922,382.

(Continued)

(51) Int. Cl.
| | |
|---|---|
| *G16H 20/13* | (2018.01) |
| *G07F 13/00* | (2006.01) |
| *G16H 40/20* | (2018.01) |
| *G07F 17/00* | (2006.01) |
| *G16H 40/67* | (2018.01) |
| *A61J 7/00* | (2006.01) |
| *G06F 21/32* | (2013.01) |
| *G06F 21/34* | (2013.01) |
| *G06K 7/00* | (2006.01) |
| *G06K 7/10* | (2006.01) |

(52) U.S. Cl.
CPC ............ *G07F 13/00* (2013.01); *A61J 7/0076* (2013.01); *G06F 21/32* (2013.01); *G06F 21/34* (2013.01); *G06K 7/0004* (2013.01); *G06K 7/10297* (2013.01); *G06K 7/10425* (2013.01); *G07F 17/0092* (2013.01); *G16H 20/13* (2018.01); *G16H 40/20* (2018.01); *G16H 40/67* (2018.01)

(58) Field of Classification Search
CPC ................................................... G07F 17/0092
See application file for complete search history.

(56) References Cited

U.S. PATENT DOCUMENTS

| 4,961,507 A | 10/1990 | Higgins |
|---|---|---|
| 6,206,238 B1 | 3/2001 | Ophardt |

(Continued)

FOREIGN PATENT DOCUMENTS

| EP | 1165010 | 1/2002 |
|---|---|---|
| EP | 1702548 A2 | 4/2002 |
| WO | 2005043469 A1 | 5/2005 |

OTHER PUBLICATIONS

International Search Report for corresponding PCT Application No. PCT/EP2017/054984, dated May 11, 2017, pp. 1-14.

*Primary Examiner* — Timothy R Waggoner
(74) *Attorney, Agent, or Firm* — Troutman Pepper Hamilton Sanders LLP (Rochester)

(57) ABSTRACT

There is described a precision dispenser for liquids, in particular medications, which allows the remote control of all operations associated with dispensing the medication to the patient so as to avoid abuses.

9 Claims, 1 Drawing Sheet

Related U.S. Application Data

(60) Provisional application No. 62/365,696, filed on Jul. 22, 2016.

(56) References Cited

U.S. PATENT DOCUMENTS

| | | | |
|---|---|---|---|
| 10,922,382 B2 * | 2/2021 | Angeli | A61J 7/0076 |
| 2004/0210341 A1 | 10/2004 | Wallace et al. | |
| 2004/0254676 A1 | 12/2004 | Blust et al. | |
| 2005/0108057 A1 | 5/2005 | Cohen et al. | |
| 2007/0186923 A1 | 8/2007 | Poutiatine et al. | |
| 2007/0233521 A1 | 10/2007 | Wehba et al. | |
| 2009/0219131 A1 | 9/2009 | Barnett et al. | |
| 2010/0042437 A1 | 2/2010 | Levy et al. | |
| 2011/0017776 A1 | 1/2011 | Metropulos et al. | |
| 2011/0047043 A1 | 2/2011 | Beane et al. | |
| 2011/0178359 A1 | 7/2011 | Hirschman et al. | |
| 2012/0004770 A1 | 1/2012 | Ooyen et al. | |
| 2013/0068790 A1 | 3/2013 | Patthey | |
| 2013/0253700 A1 | 9/2013 | Carson et al. | |
| 2013/0317753 A1 | 11/2013 | Kamen et al. | |
| 2014/0121845 A1 | 5/2014 | Mueller | |
| 2014/0156064 A1 | 6/2014 | Crawford et al. | |
| 2014/0339248 A1 | 11/2014 | Reddy et al. | |

\* cited by examiner

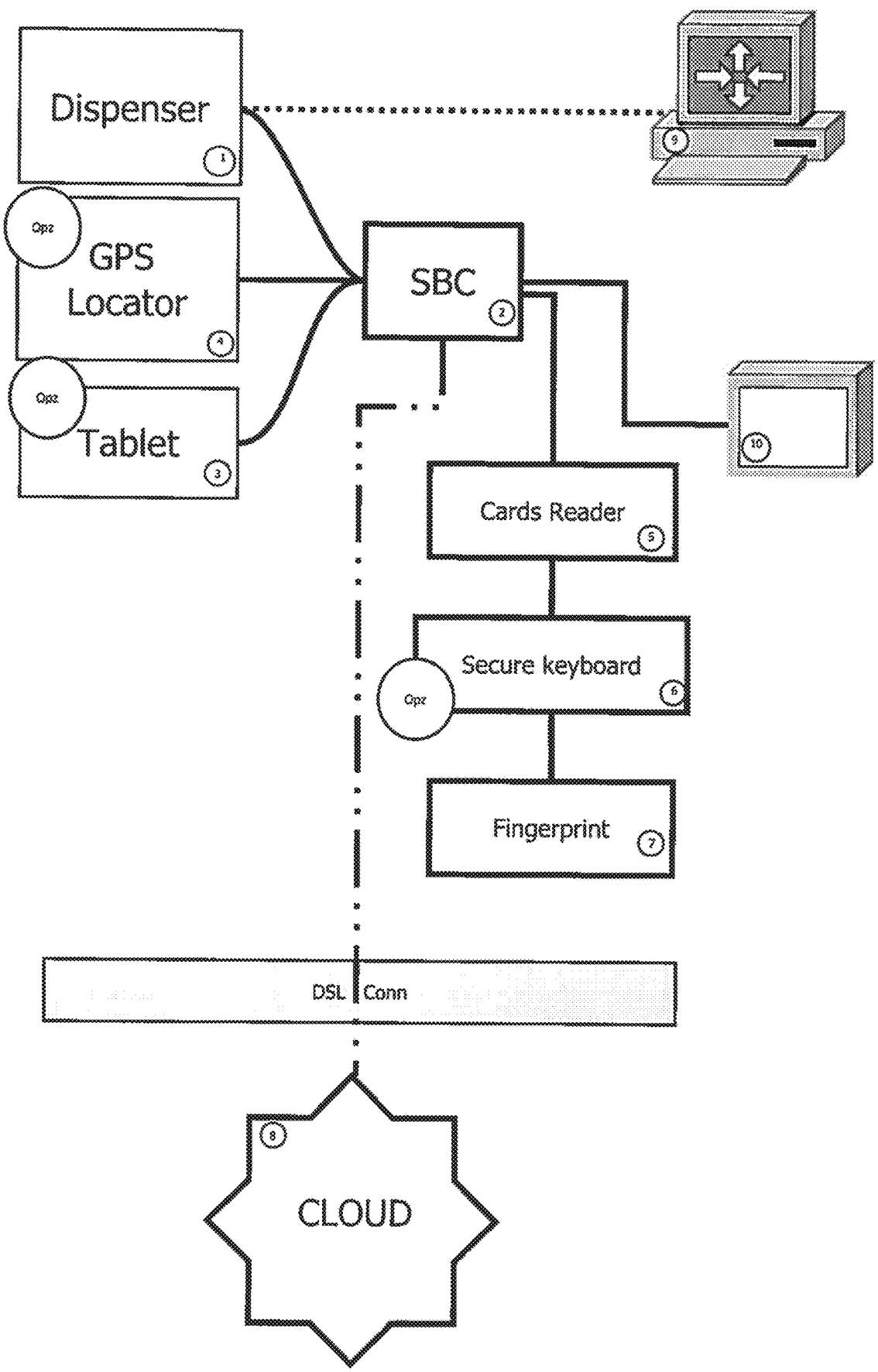

PRECISION DISPENSER FOR LIQUIDS, COMPRISING A DEVICE FOR REMOTE CONTROL AND MONITORING

This application is a continuation of U.S. patent application Ser. No. 15/446,809, filed Mar. 1, 2017, which claims the benefit of U.S. Provisional Patent Application Ser. No. 62/365,696 filed Jul. 22, 2016 which is hereby incorporated by reference in its entirety.

FIELD

The present invention relates to the field of precision dispensers for liquids, in particular liquid pharmaceutical compositions.

BACKGROUND

As is known, certain pharmaceutical compositions in liquid form are administered through dispensers that dispense the amount required as indicated by the general practitioner.

The problems associated with dispensing precision have already been studied since long and overcome by means of various devices such as for example the automatic liquid dispenser patented by the same Applicant (see EP 1 165 010).

However, when the pharmaceutical compositions, due to their nature, may cause wrongful behavior by the user or third parties (e.g. in case of methadone or other medicaments for treating drug addiction), absolute control not only on the amount but on the general conditions of delivery become essential.

Currently, devices for dispensing liquids, and more specifically medicaments in liquid form requiring increased and monitored dispensing precisions, are for the most part apparatuses monitored locally by a PC which is given the bureaucratic task of recording the data according to the local laws and of controlling the system by taking the information from its memory and dispensing the amount prescribed.

It is therefore evident the importance of an apparatus which not only allows to monitor and dispense the liquid with extreme precision, but also prevents improper use of the medicament administered without the mandatory presence of operators at the medicament distribution site, which would obviously be unfeasible for practical reasons.

SUMMARY

It is describe a precision dispenser for liquids, in particular medicament, that allows the remote control of all the operations associated with dispensing the medicament to the patient so as to avoid abuses.

BRIEF DESCRIPTION OF THE DRAWINGS

The accompanying FIG. 1 shows schematically a device according to the invention.

DETAILED DESCRIPTION

The present invention allows to overcome the aforesaid problems by means of a precision dispenser for liquids, comprising means capable of interfacing with a remote data server which provides the information required to manage the controlled dispensing of the medicament through a preliminary identification of the user, verifying that the user does not attempt to take more than his/her prescribed dose by going to other dispensing centers in a short time.

On the other hand, the system also allows the patient to access the dose of medicament required at any center equipped with a device according to the invention, with significant advantages not only for the patient but also for the whole national care service, since it would no longer be necessary to deliver the medicament at patient's home.

The device according to the invention also allows to have all the users' data at the dispensing centers in a particular country to be arranged in a centralized manner and under secure computer technology, this allowing to use this information for assessments and statistical reports on the user population, understanding better the regional needs and distribution thereof, and managing samples of population in order to improve and/or expand the care service.

In particular, in accordance with the present invention, the above said precision dispenser comprises:
- contact or contactless (c-less) card/tag/chip readers;
- any security keyboards for the patient to introduce his/her PIN;
- recognition readers;
- any GPS position detection systems;
- an SBC (Single Board Computer) unit capable of interfacing the above devices and of connecting to the central management system in wired, wireless (Wi-Fi) mode or through the telephone network.

As seen in the accompanying FIGURE, the device according to the invention comprises a pharmacological substance dispenser 1 of known type, equipped with a hydraulic and electronic control system for performing its function.

Said function is controlled by an external processor 9 which contains the using profiles of all patients, the amounts of medication to be administered, their therapeutic protocol, etc.

Dispenser 1 is then interfaced with a device 2 (SBC) capable of operating autonomously and equipped with RAM and EEPROM memory, and also with an SSD disc, standard interfaces capable of accommodating expansions of various nature, including for example Wi-Fi.

Dispenser 1 is equipped with a card reader 5, possibly a secure keyboard 6, a recognition reader 7 and a monitor 10 (possibly touch-screen).

The card reader 5 is a device of known type capable of reading (contact or contactless) cards or tags, which allow the registration of the users, and therefore their first-level identification.

The secure keyboard 6 allows a PIN (Personal Identification Number) to be entered, thus allowing the second-level identification of the user if required.

The recognition reader 7 may be, for example, a fingerprint reader or a facial recognition reader (or other similar device), and allows the second- or third-level identification (depending on whether or not the secure keyboard is used).

The reader allows to read the fingerprint (or the face and/or iris, respectively) of the user when acquiring the identity of the user, while it is used as a validation instrument when checking his/her identity by comparing it with the data recorded by the system.

The touchscreen monitor 10 (Man Machine Interface) allows the dialogue between the user of the device and the machine, and displays the output and receives the inputs of the APPs running on the SBC (2) for acquiring the identity data and checking them after the check with the network, as explained hereinbelow.

Card reader 5, secure keyboard 6 and recognition reader all interface with device 2 (SBC).

Moreover, if desired, dispenser 1 may be interfaced with a tablet 3 (integrated therein or connected externally) which allows to analyze data and remotely monitor the device, especially by healthcare personnel.

If required, dispenser 1 may also be interfaced with a GPS position detector which allows the position of the dispensing center (e.g. if it is mobile) to be detected in real time by means of the SBC device above.

All the above-described devices allow the unambiguous and secure identification of the patient in order to ensure the correct dispensing of the medication according to the treatment plan established for him/her by the healthcare personnel.

Said identification occurs for example when the user requests the medication to be dispensed by providing a contactless card and with the acquisition of the fingerprint or the facial verification.

Suitable and known multimedia communication modes (e.g. connection to the network, all types of possible wired connections or those supported by the telephone or satellite network) are used to transfer this information to a WEB application, normally a CLOUD-based application, which records and stores the information in real time. These data, together with the treatment information related to the medication dispensing event, are read in the other direction through queries to the Database Server in order to ensure there are no attempts to make double dispensing requests, performed for example in a different medication dispensing center within a given period of time.

As noted in FIG. 1, the system is obviously mediated by a DSL interface (ADSL, XDSL or analogue connections), which allows the connection to the CLOUD and accordingly the two-way log in between all devices installed in the medication dispensing centers and the Web Server Application installed on the Cloud.

As indicated above, the system is capable of operating autonomously through the SBC, but a connection of dispenser 1 to a PC 9 may be provided, if required, thus taking advantage of an API control interface to control the dispensing activities and the local registrations, as well as the management of the activities of transferring the medications according to the local regulations and the reporting activities in compliance with the legal regulations of the country where the apparatus is installed, at the end of the daily session.

What is claimed is:

1. A liquid medicament dispenser device comprising:
   a liquid medicament precision dispenser comprising a hydraulic and electronic control system configured to be operated by a remote computing device external to the liquid medicament precision dispenser to dispense pre-determined doses of a liquid medicament, at an accuracy within 0.5% by volume of the pre-determined doses, to a plurality of patients based on a therapeutic protocol established by a healthcare provider for each of the plurality of patients;
   a patient identification device integrated with the liquid medicament dispenser; and
   a computing device external to and remotely coupled to the liquid medicament dispenser, the computing device being connected via one or more communication networks to a remote web-based server storing an identification profile comprising the therapeutic profile for each of the plurality of patients, the computing device comprising a processor and a memory coupled to the processor which is configured to execute one or more programmed instructions comprising and stored in the memory to:
   receive a patient request from one of the plurality of patients for authorization to dispense the predetermined dose of the liquid medicament at the patient identification device, wherein each of the plurality of patients are authorized to receive the liquid medicament from a plurality of liquid medicament dispensers in a plurality of geographical locations;
   transfer the patient request via the one or more communication networks to the remote web-based server;
   provide instructions to control the hydraulic and electronic control system of the liquid medicament dispenser to dispense the pre-determined dose of the liquid medicament upon a receipt of an authorization from the web-based server based on the patient request; and
   provide instructions to the liquid medicament dispenser not to dispense the pre-determined dose of the liquid medicament upon receipt of a non-authorization from the web-based server, wherein the non-authorization is based on an attempt by the one of the plurality of patients to obtain more than the pre-determined dose of the liquid medicament from another of the plurality of liquid medicament dispensers within a period of time;
   wherein said liquid medicament is a medicament requiring strict administration control.

2. The device according to claim 1, further comprising a tablet computing device integrated to the liquid medicament dispenser device and the computing device.

3. The device according to claim 1, wherein the patient identification device comprises one or more of a reader device, a secure keyboard, a patient recognition reader, or a touchscreen.

4. The device according to claim 3, wherein the reader device is a contact or contactless card, tag, or chip reader, or a magnetic card reader.

5. The device according to claim 4, wherein the patient recognition reader is a facial reader or a fingerprint reader.

6. The device according to claim 1, wherein the computing device is a single board computing device.

7. The device according to claim 1, wherein the liquid medicament dispenser is interfaced to a GPS position detector through the computing device.

8. A method for controlling and monitoring dispensing liquid medicament to a patient comprising:
   receiving, by a computing device external and remotely coupled to a liquid medicament precision dispenser comprising a hydraulic and electronic control system configured to be operated by the remote computing device external to the liquid medicament precision dispenser to dispense pre-determined doses of liquid medicament, at an accuracy within 0.5% by volume of the pre-determined doses, to a plurality of patients based a therapeutic protocol established by a healthcare provider for each of the plurality of patients and connected via one or more communication networks to a remote web-based server storing an identification profile comprising the therapeutic profile for each of the plurality of patients, a patient request for authorization to dispense the liquid medicament at a patient authorization device integrated with the liquid medicament dispenser upon receipt of the patient request for authorization to dispense the liquid medicament, wherein each of the plurality of patients are authorized to receive the liquid medicament from a plurality of the liquid medicament dispensers in a plurality of geographical locations;

transferring, by the computing device, the patient request via the one or more communication networks to the remote web-based server;

providing, by the computing device, instructions to control the hydraulic and electronic control system of the liquid medicament dispenser to dispense the pre-determined dose of the liquid medicament upon a receipt of an authorization from the web-based server based on the patient request; and providing, by the computing device, instructions to the liquid medicament dispenser not to dispense the pre-determined dose of the liquid medicament upon receipt of a non-authorization from the web-based server, wherein the non-authorization is based on an attempt by the one of the plurality of patients to obtain more than the pre-determined dose of the liquid medicament from another of the plurality of liquid medicament dispensers within a period of time;

wherein said liquid medicament is a medicament requiring strict administration control.

9. A system comprising:

a web-based server storing an identification profile comprising a therapeutic profile for each of a plurality of patients;

a plurality of liquid medicament precision dispenser devices located in a plurality of geographic locations, each of the plurality of liquid medicament precision dispenser devices comprising:

a liquid medicament precision dispenser comprising a hydraulic and electronic control system configured to be operated by a remote computing device external to the liquid medicament precision dispenser to dispense pre-determined doses of liquid medicament, at an accuracy within 0.5% by volume of the pre-determined doses, to a plurality of patients based on a therapeutic protocol established by a healthcare provider for each of the plurality of patients;

a patient identification device integrated with the liquid medicament dispenser; and a computing device external to and remotely coupled to the liquid medicament dispenser, the computing device being connected via one or more communication networks to the web-based server, the computing device comprising a processor and a memory coupled to the processor which is configured to execute one or more programmed instructions comprising and stored in the memory to:

receive a patient request from one of the plurality of patients for authorization to dispense the predetermined dose of the liquid medicament at the patient identification device, wherein each of the plurality of patients are authorized to receive the liquid medicament from the plurality of liquid medicament dispensers in the plurality of geographic locations;

transfer the patient request via one or more communication networks to the web-based server;

provide instructions to control the hydraulic and electronic control system of the liquid medicament dispenser to dispense the pre-determined dose of the liquid medicament upon a receipt of an authorization from the web-based server based on the patient request; and provide instructions to the liquid medicament dispenser not to dispense the pre-determined dose of the liquid medicament upon receipt of a non-authorization from the web-based server, wherein the non-authorization is based on an attempt by the one of the plurality of patients to obtain more than the pre-determined dose of the liquid medicament from another of the plurality of liquid medicament dispensers within a period of time;

wherein said liquid medicament is a medicament requiring strict administration control.

\* \* \* \* \*